United States Patent [19]

Reiffenrath et al.

[11] Patent Number: 5,248,447

[45] Date of Patent: Sep. 28, 1993

[54] 2,3-DIFLUOROHYDROQUINONE DERIVATIVES

[75] Inventors: Volker Reiffenrath, Rossdorf; Joachim Krause, Dieburg; Andreas Wächtler, Griesheim; Georg Weber, Erzhausen; Thomas Geelhaar, Mainz, all of Fed. Rep. of Germany; David Coates, Merley, Wimborne, United Kingdom; Ian C. Sage, Broadstone, United Kingdom; Simon Greenfield, Creekmoor, Poole, United Kingdom

[73] Assignee: Merck Patent Gesellschaft mit beschrankter Haftung, Darmstadt, Fed. Rep. of Germany

[21] Appl. No.: 871,620

[22] PCT Filed: Feb. 27, 1989

[86] PCT No.: PCT/EP89/00179

§ 371 Date: May 15, 1989

§ 102(e) Date: May 15, 1989

[87] PCT Pub. No.: WO89/08637

PCT Pub. Date: Sep. 21, 1989

Related U.S. Application Data

[63] Continuation of Ser. No. 362,435, May 15, 1989, abandoned.

[30] Foreign Application Priority Data

Mar. 10, 1988 [DE] Fed. Rep. of Germany ....... 3807801

[51] Int. Cl.$^5$ .................. C09K 19/30; C07C 69/76; C07C 41/00
[52] U.S. Cl. .................. 252/299.63; 252/299.67; 560/59; 560/62; 560/63; 568/645; 568/649; 568/656; 359/103
[58] Field of Search ........... 252/229.1, 299.61, 299.62, 252/299.67, 299.68; 568/631, 644, 645, 648, 649, 656; 560/57, 59, 62, 63; 359/103

[56] References Cited

U.S. PATENT DOCUMENTS

| | | | |
|---|---|---|---|
| 4,279,770 | 7/1981 | Inukai et al. | 252/299.62 |
| 4,366,330 | 12/1982 | Gray et al. | 568/775 |
| 4,368,135 | 1/1983 | Osman | 252/299.63 |
| 4,415,470 | 11/1983 | Eidenschink et al. | 252/299.63 |
| 4,514,317 | 4/1985 | Tuong et al. | 252/299.62 |
| 4,545,922 | 10/1985 | Eidenschink et al. | 252/299.63 |
| 4,551,264 | 11/1985 | Eidenschink et al. | 252/299.61 |
| 4,602,851 | 7/1986 | Jenner et al. | 252/299.63 |
| 4,606,845 | 8/1986 | Romer et al. | 252/299.63 |
| 4,621,901 | 11/1986 | Petrzilka et al. | 350/350 R |
| 4,637,897 | 1/1987 | Kelly | 252/299.63 |
| 4,659,502 | 4/1987 | Fearon et al. | 252/299.61 |
| 4,664,840 | 5/1987 | Osman | 252/299.63 |
| 4,710,315 | 12/1987 | Schad et al. | 252/299.63 |
| 4,724,097 | 2/1988 | Romer et al. | 252/299.63 |
| 4,753,752 | 6/1988 | Raynes et al. | 252/299.65 |
| 4,776,973 | 10/1988 | Bofinger et al. | 252/299.61 |
| 4,820,839 | 4/1989 | Krause et al. | 252/299.01 |
| 4,834,904 | 5/1989 | Krause et al. | 252/299.01 |
| 4,874,544 | 10/1989 | Yong et al. | 252/299.61 |
| 4,897,216 | 1/1990 | Reiffenrath et al. | 252/299.63 |
| 4,911,863 | 3/1990 | Sage et al. | 252/299.65 |
| 4,925,278 | 5/1990 | Buchecker et al. | 252/299.01 |
| 4,925,590 | 5/1990 | Reiffenrath et al. | 282/299.61 |
| 4,986,931 | 1/1991 | Eidenschink et al. | 252/299.63 |
| 5,087,764 | 2/1992 | Reiffenrath et al. | 568/656 |

FOREIGN PATENT DOCUMENTS

| | | |
|---|---|---|
| 0051738 | 3/1981 | European Pat. Off. |
| 0084194 | 7/1983 | European Pat. Off. |
| 0133489 | 7/1984 | European Pat. Off. |
| 2429093 | 1/1975 | Fed. Rep. of Germany |
| 2939782 | 4/1981 | Fed. Rep. of Germany ........ 252/299.64 |
| WO88/02130 | 3/1988 | World Int. Prop. O. |

Primary Examiner—Robert L. Stoll
Assistant Examiner—Shean C. Wu
Attorney, Agent, or Firm—Millen, White, Zelano & Branigan

[57] ABSTRACT

2,3-difluorohydroquinone compounds of the formula I (Abstract continued on next page.)

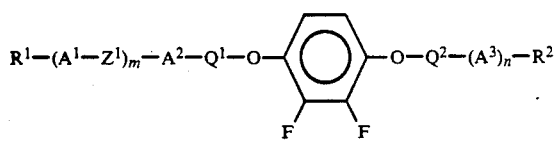

in which
R$^1$ and R$^2$, in each case independently of one another, are alkyl having 1 to 15 C atoms or alkenyl having 3 to 15 C atoms which are unsubstituted, monosubstituted by cyano or at least monosubstituted by fluorine or chlorine, it also being possible for one CH$_2$ group in these radicals to be replaced by —O—, —CO—, —CO—O—, —O—CO— or —O—CO—O—, A$^1$, A$^2$ and A$^3$, in each case independently of one another, are
(a) trans-1,4-cyclohexylene, in which, in addition, one or two non-adjacent CH$_2$ groups may be replaced by —O— and/or —S—,
(b) 1,4-phenylene, in which, in addition, one or two CH groups may be replaced by N, or
(c) a radical from the group comprising piperidine-1,4-diyl, 1,4-bicylo (2,2,2)-octylene (sic), 1,3,4-thiadiazole-2,5-diyl, napththalene-2,6-diyl, decahydronaphthalene-2,6-diyl and 1,2,3,4-tetrahydronaphthalene-2,6-diyl, it being possible for the radicals (a) and (b) to be monosubstituted or polysubstituted by F, Cl, CH$_3$ or CN, Z$^1$ is —CO—O—, —O—CO—, —CH$_2$CH$_2$—, —OCH$_2$—, —CH$_2$O—, —C≡C— or a single bond, Q$^1$ and Q$^2$, in each case independently of one another, are —CO— or —CH$_2$—, m and n are each 0, 1 or 2, and
(m+n) is 0, 1 or 2, are suitable as components of liquid-crystalline phases.

13 Claims, No Drawings

2,3-DIFLUOROHYDROQUINONE DERIVATIVES

This application is a continuation of application Ser. No. 07/362,435, filed May 15, 1989 now abandoned.

SUMMARY OF THE INVENTION

The invention relates to 2,3-difluorohydroquinone derivatives of the formula I

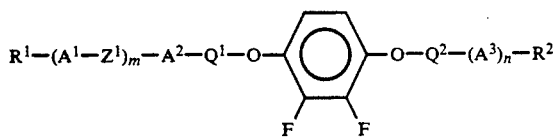

in which $R^1$ and $R^2$, in each case independently of one another, are alkyl having 1 to 15 C atoms or alkenyl having 3 to 15 C atoms which are unsubstituted, monosubstituted by cyano or at least monosubstituted by fluorine or chlorine, it also being possible for one $CH_2$ group in these radicals to be replaced by —O—, —CO—, —CO—O—, —O—CO— or —O—CO—O—,

EXAMPLES $A^1$, $A^2$ and $A^3$, in each case independently of one another, are
(a) trans-1,4-cyclohexylene, in which, in addition, one or two non-adjacent $CH_2$ groups may be replaced by —O— and/or —S—,
(b) 1,4-phenylene, in which, in addition, one or two CH groups may be replaced by N, or
(c) a radical from the group comprising piperidine-1,4-diyl, 1,4-bicylo-(2,2,2)octylene (sic), 1,3,4-thiadiazole-2,5-diyl, napththalene-2,6-diyl, decahydronaphthalene-2,6-diyl and 1,2,3,4-tetrahydronaphthalene-2,6-diyl, it being possible for the radicals (a) and (b) to be monosubstituted or polysubstituted by F, Cl, $CH_3$ or CN, $Z^1$ is —CO—O—, —O—CO—, —$CH_2$—$CH_2$—, —$OCH_2$—, —$CH_2O$—, —C≡C— or a single bond, $Q^1$ and $Q^2$, in each case independently of one another, are —CO— or —$CH_2$—, m and n are each 0, 1 or 2, and (m+n) is 0, 1 or 2.

For reasons of simplicity, Cyc below is a 1,4-cyclohexylene group and $PheF_2$ below is a group of the formula

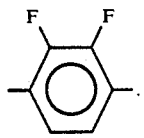

The compounds of the formula I can be used as components of liquid-crystalline media, in particular for displays based on the principle of the twisted cell, the guest-host effect, the effect of deformation of aligned phases or the effect of dynamic scattering.

The compounds of the formula I are distinguished by a clearly negative anisotropy of the dielectric constant and, in an electrical field, are aligned with their longitudinal molecular axes perpendicular to the field direction.

This effect is known and is utilized to control the optical transparency in various liquid-crystal displays, for example in liquid-crystal cells of the light-scattering type (dynamic scattering), of the so-called DAP type (deformation of aligned phases) or ECB type (electrically controlled birefrigence) or of the guest/host type (guest/host interaction).

The compounds of the formula I are also suitable as components of nematic or chirally nematic liquid-crystalline media having a dielectric anisotropy which is positive overall. The purpose of the compounds of the formula I here is to increase $\epsilon_{195}$. The negative dielectric anisotropy of the compounds according to the invention is overcompensated here by addition of components which are highly positive dielectrically. Such media are used for TN displays having a 90° twist or, in particular, for more highly twisted TN cells since they result here in particularly steep characteristic lines.

In addition, compounds of the formula I are suitable as components of chiral tilted smectic media. Chiral tilted smectic liquid-crystalline media having ferroelectric properties can be prepared by adding a suitable chiral dope to base mixtures containing one or more tilted smectic media (L. A. Veresnev et al., Mol. Cryst. Liq. Cryst. 89, 327 (1982); H. R. Brand et al., J. Physique 44 (lett.), L-771 (1983). Such media can be used as dielectrics for rapidly switching displays based on the principle, described by Clark and Lagerwall, of SSFLC technology (N. A. Clark and S. T. Lagerwall, Appl. Phys. Lett. 36, 899 (1980); U.S. Pat. 4,367,924) on the basis of the ferroelectric properties of the chiral tilted medium.

A number of liquid-crystalline compounds having slightly negative dielectric anisotropy have hitherto already been synthesized. In contrast, only relatively few liquid-crystal components having a large negative anisotropy of the dielectric constant are known. In addition, the latter generally have disadvantages, such as, for example, poor solubility in mixtures, high viscosity, high melting points and chemical instability. There is therefore a demand for further compounds having negative dielectric anisotropy which permit the properties of mixtures to be further improved for a very wide variety of electrooptical applications.

Liquid-crystal compounds having a negative dielectric anisotropy and containing two or three rings linked via carboxyl groups or a covalent bond and containing one or more side groups, such as halogen, cyano or nitro groups, are known from DE 2,240,864, DE 2,613,293, DE 2,835,662, DE 2,836,086 and EP 023,728.

EP 084,194 gives a broad formula covering the compounds claimed here. However, no individual compounds of the formula according to the invention are mentioned. Those skilled in the art would thus be able neither to deduce in simple manner possible syntheses for the compounds claimed nor to recognize that the compounds according to the invention have mesophase regions which are predominantly in a favorable location and are distinguished by a large negative anisotropy of the dielectricity with at the same time low viscosity.

Neither is there any indication of the possibility of using the compounds according to the invention in the displays based on SSFLC technology, since the compounds claimed therein have low smectic tendencies.

Furthermore, dibenzoic acid esters of 2,3-dichlorohydroquinone are known (for example Bristol et al., J. Org. Chem. 39, 3138 (1974) or Clanderman et al., J. Am. Chem. Soc. 97, 1585 (1975)), but these are monotropic or have very small mesophase ranges. The esters of 4-hydroxy-2,3-dichlorobenzoic acid described by Eidenschink et al. (Angew. Chem. 89, 103 (1977)) likewise have only narrow mesophase ranges.

The 4-alkyl-2,3-dichlorophenyl-4'-alkylbicyclohexyl-4-carboxylic acid esters known from German Offenlegungsschrift 2,933,563 cannot be used industrially due to their high viscosity.

The invention had the object of indicating stable, liquid-crystalline or mesogenic compounds having a large negative anisotropy of the dielectricity and simultaneously low viscosity.

It has been found that the compounds of the formula I are preeminently suitable as components of liquid-crystalline media. They can be used, in particular, to prepare stable liquid-crystalline media having a broad mesophase range and comparatively low viscosity.

The compounds of the formula I are furthermore suitable as components of chiral tilted smectic liquid-crystalline media.

In addition, the provision of compounds of the formula I very generally considerably broadens the range of liquid-crystalline substances which are suitable, from various applicational points of view, for the purpose of preparing liquid-crystalline media.

The compounds of the formula I have a broad field of application. Depending on the choice of substituents, these compounds can be used as base materials from which liquid-crystalline media are predominantly composed; however, it is also possible to add liquid-crystalline base materials from other classes of compounds to the compounds of the formula I in order, for example, to vary the dielectric and/or optical anisotropy and/or viscosity and/or the spontaneous polarization and/or the phase ranges and/or the tilt angle and/or the pitch of a dielectric of this type.

The compounds of the formula I are furthermore suitable as intermediates for the preparation of other substances which can be used as components of liquid-crystalline media.

In the pure state, the compounds of the formula I are colorless and form liquid-crystalline mesophases in a temperature range in a favorable location for electro-optical use. They are very stable chemically, thermally and to light.

The invention thus relates to the compounds of the formula I and to a process for their preparation, characterized in that an appropriate carboxylic acid or hydroxyl compound or a reactive derivative thereof is reacted with an appropriate hydroxyl compound or a reactive derivative thereof.

The invention additionally relates to the use of the compounds of the formula I as components of liquid-crystalline media. The invention furthermore relates to liquid-crystalline media containing at least one compound of the formula I, and to liquid-crystal display elements containing such media. Media of this type have particularly advantageous elastic constants, and, due to their low $\Delta\epsilon/\epsilon_\perp$ values, are particularly suitable for TFT mixtures.

The invention furthermore relates to all novel intermediates for the preparation of the compounds according to the invention.

Above and below, $R^1$, $R^2$, $A^1$, $A^2$, $A^3$, $Z^1$, $Q^1$, $Q^2$, n and m are as defined, unless expressly stated otherwise.

The compounds of the formula I accordingly include preferred compounds having two rings, of the sub-formula Ia:

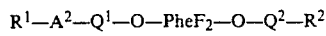

preferred compounds having three rings, of the sub-formulae Ib to Id:

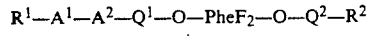

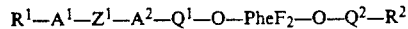

and preferred compounds having four rings, of the sub-formulae Ie and If:

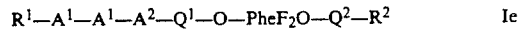

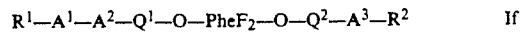

Of these, the compounds of the sub-formulae Ia, Ib and Ic are particularly preferred.

In the compounds of the formulae above and below, $R^1$ and $R^2$ are preferably alkyl or alkoxy.

Additionally preferred compounds are those of the formulae above and below in which one of the radicals $R^1$ and $R^2$ is alkenyl or oxaalkyl (for example alkoxymethyl).

In the formulae above and below, $R^1$ and $R^2$ preferably have 2–12 C atoms, in particular 3–10 C atoms. It is also possible for one or two $CH_2$ groups in $R^1$ and $R^2$ to have been replaced. It is preferred that only one $CH_2$ group has been replaced, by —O— or —CH=CH—.

In the formulae above and below, $R^1$ and $R^2$ are preferably alkyl, alkoxy or another oxaalkyl group, furthermore also alkyl groups in which one or two $CH_2$ groups may be replaced by —CH=CH—.

If $R^1$ and $R^2$ are alkyl radicals in which, in addition, one ("alkoxy" or "oxaalkyl") or two ("alkoxyalkoxy" or "dioxaalkyl") non-adjacent $CH_2$ groups may be replaced by O atoms, they can be straight-chain or branched. They are preferably straight-chain, have 2,3,4,5,6 or 7 C atoms and are accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxypropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-, 3,6- or 4,6-dioxaheptyl.

If $R^1$ and $R^2$ are an alkyl radical in which one $CH_2$ group has been replaced by —CH=CH—, the trans form is preferred. This alkenyl radical can be straight-chain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If the radicals $R^1$ and $R^2$ are monosubstituted by cyano or at least monosubstituted by fluorine or chlorine, they are preferably ω-fluoro- or ω-cyano-n-alkyl having 1-12 C atoms, n-alkyl groups having 2-12 C atoms with substitution by fluorine, chlorine or cyano on a secondary C atom, or perfluoro-n-alkyl groups having 1-12 C atoms in which, in addition, one or more $CF_2$ groups may be replaced by —O— and/or —$CH_2$—.

Compounds of the formula I having branched wing groups $R^1$ and/or $R^2$ may occasionally be of importance due to better solubility in the customary liquid-crystalline base materials, but in particular as chiral dopes if they are optically active. Smectic compounds of this type are suitable as components for ferroelectric materials.

Branched groups of this type generally contain not more than one chain branch. Preferred branch radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, -2methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl and 6-methyloctoxy.

The formula I covers the racemates of these compounds and the optical antipodes, and mixtures thereof.

$A^1$, $A^2$ and $A^3$, in each case independently of one another, are preferably trans-1,4-cyclohexylene, 1,4-phenylene, 2- or 3-fluoro-1,4-phenylene, 2,3-difluoro-1,4-phenylene, pyrimidine-2,5-diyl or pyridine-2,5-diyl. The compounds according to the invention preferably contain only one 2-fluoro-1,4-phenylene, 3-fluoro-1,4-phenylene, pyridine-2,5-diyl or pyrimidine-2,5-diyl group. Particularly preferred meanings for $A^1$, $A^2$ and $A^3$ are trans-1,4-cyclohexylene and 1,4-phenylene.

m and n are each preferably 0 or 1. $Z^1$ is preferably —$CH_2CH_2$— or a single bond. $Q^1$ is —CO— or —$CH_2$— in the case where $A^2$=radical (a) [i.e. for example, 1,4-cyclohexylene]; —$CH_2$— being preferred. In the case where $A^2$=radical (b) [i.e. for example, 1,4-phenylene], $Q^1$ is preferably —CO—.

Of the compounds of the formulae I and Ia to If, those are preferred in which at least one of the radicals present therein has one of the preferred meanings indicated.

Particularly preferred compounds are 2,3-difluorohydroquinone derivatives of the formula Ia':

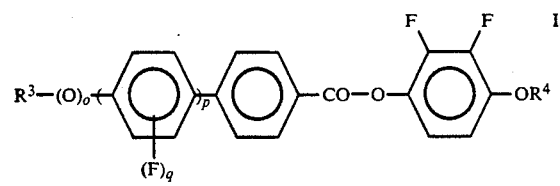

in which $R^3$ and $R^4$, in each case independently of one another, are alkyl having 1 to 15 C atoms, and o, p and q are 0 or 1, and 2,3-difluorohydroquinone derivatives of the formula Ia''

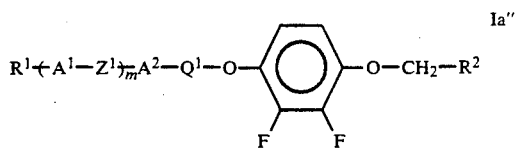

in which $R^1$, $R^2$ and $Q^1$ have the meaning indicated in claim 1, m is 0 or 1, $Z^1$ is —$CH_2CH_2$— or a single bond, Al and $A^2$ are each trans-1,4-cyclohexylene.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use can also be made here of variants which are known per se, but are not described in greater detail here.

If desired, the starting materials can also be formed in situ by not isolating them from the reaction mixture, but instead immediately converting them further into the compounds of the formula I.

The compounds of the formula I are accessible starting from 1,2-difluorobenzene. The latter is metallated by a process known per se (for example A. M. Roe et al., J. Chem. Soc. Chem. Comm., 22, 582 (1965)), and the metallation product is reacted with the appropriate electrophile. This reaction sequence can be carried out a second time using the 1-substituted 2,3-difluorobenzene obtained in this way, for example using tert.-butylhydroperoxide as the electrophile, and the 1-substituted 2,3-difluorophenols are thus obtained. 1,2-difluorobenzene or 1-substituted 2,3-difluorobenzene is reacted with phenyllithium, lithium tetramethylpiperidine, n-, sec- or tert-butyllithium at temperatures of from −100° C. to +50° C., preferably −78° C. to 0° C., in an inert solvent, such as diethyl ether, tetrahydrofuran, dimethoxyethane, tert-butyl methyl ether or dioxane, hydrocarbons, such as hexane, heptane, cyclohexane, benzene or toluene, or mixtures of these solvents, if appropriate with the addition of a complexing agent, such as tetramethylethylenediamine (TMEDA) or hexamethylphosphoric triamide.

The lithium-2,3-difluorophenyl compounds are reacted with the appropriate electrophiles at −100° C. to 0° C., preferably at −50° C. Suitable electrophiles are aldehydes, ketones, nitriles, epoxides, carboxylic acid derivatives, such as esters, anhydrides or halides, haloformic acid esters or carbon dioxide.

For reaction with aliphatic or aromatic halogen compounds, the lithium 2,3-difluorophenyl compounds are transmetallated and coupled with transition-metal catalysis. Zinc 2,3-difluorophenyl compounds (cf. German Offenlegungsschrift 3,632,410) or titanium 2,3-difluorophenyl compounds (cf. German Offenlegungsschrift 3,736,489) are particularly suitable for this purpose.

The compounds of the formula I can be prepared by esterification of appropriate carboxylic acids (or reactive derivatives thereof) using alcohols or phenols (or reactive derivatives thereof).

Suitable reactive derivatives of the carboxylic acids mentioned are, in particular, the acid halides, above all the chlorides and bromides, furthermore the anhydrides, for example also mixed anhydrides, azides or esters, in particular alkyl esters having 1-4 C atoms in the alkyl group.

Suitable reactive derivatives of the alcohols or phenols mentioned are, in particular, the corresponding metal alcoholates or phenolates, preferably of an alkali metal such as Na or K.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons such as benzene, toluene or xylene, halogenated hydrocarbons, such as carbon tetrachloride or tetrachloroethylene, and sulphoxides, such as dimethyl sulphoxide or sulpholane. Water-immiscible solvents can advantageously be used at the same time for removal of the water formed during the esterification by azeotropic distillation. An excess of an organic base, for example pyridine, quinoline or triethylamine, can occasionally also be used as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reaction is generally complete after 15 minutes to 48 hours.

In detail, the reaction conditions for the esterification depend substantially on the nature of the starting materials used. Thus, the reaction of a free carboxylic acid with a free alcohol or phenol is generally carried out in the presence of a strong acid, for example a mineral acid such as hydrochloric acid or sulphuric acid. A preferred reaction procedure is to react an acid anhydride or, in particular, an acyl chloride with an alcohol, preferably in a basic medium, important bases being, in particular, alkali metal hydroxides, such as sodium hydroxide or potassium hydroxide, alkali metal carbonates or hydrogen carbonates, such as sodium carbonate, sodium hydrogen carbonate, potassium carbonate or potassium hydrogen carbonate, alkali metal acetates, such as sodium acetate or potassium acetate, alkaline earth metal hydroxides, such as calcium hydroxide, or organic bases such as triethylamine, pyridine, lutidine, collidine or quinoline. A further preferred embodiment of esterification is to first convert the alcohol or the phenol, for example by treatment with ethanolic sodium hydroxide solution or potassium hydroxide solution, into the sodium alcoholate or phenolate or potassium alcoholate or phenolate, to isolate and suspend the latter with stirring in acetone or diethyl ether together with sodium hydrogen carbonate or potassium carbonate, and to add a solution of the acyl chloride or acid anhydride in diethyl ether, acetone or DMF to this suspension, expediently at temperatures between about $-25°$ and $+20°$.

The methyl ethers of the formula I can be prepared by known etherification reactions, for example by reacting a compound of the formula $R—^1—(A^1—Z^1—)_m—A^2—Q^1—O—PheF_2—Z_A$ or $R^2—(A^3)_n—Q^2—O—PheF_2—Z_A$, in which $Z_A$ is OH or OMe, SH or SMe where Me is an equivalent of a metal cation, and Hal is a halogen atom, preferably chlorine or bromine (reactive derivative of the phenols), with a compound of the formula $R^2-(A^3)_n—Z_B$ or $R^1—(A^1—Z^1—)_m—A^2—Z_B$ in which $Z_B$ is $—CH_2—OH$ or $—CH_2$-Hal (reactive derivative) in the presence of a base. In these formulae, the radicals $R^1$, $R^2$, $A^1$, $A^2$, $A^3$, $Z^1$, m, n, $Q^1$ and $Q^2$ have the meanings indicated in the formula I. The reaction conditions for these ether syntheses are those customary for such reactions; the solvents used are polar, aprotic solvents, for example dimethyl sulphoxide, N,N-dimethylformamide or N-methypyrrolidone; the bases used are preferably alkali metal salts of weak acids, for example sodium acetate, potassium carbonate or sodium carbonate. The reactions can be carried out at temperatures between 0° C. and the boiling point of the lowest-boiling component of the reaction mixture; it has proven particularly advantageous to use temperatures between 60° and 120° C. Some of the starting materials are known, and some can be prepared analogously to known compounds by standard methods of synthetic organic chemistry.

An important novel intermediate in the synthesis of compounds according to the invention is 2,3-difluorohydroquinone. This novel compound, which is likewise subject-matter of the invention, can be obtained by oxidation of the known 2,3-difluorophenol in a manner known per se, for example by oxidation using potassium peroxodisulphate in alkaline, aqueous solution.

In addition to one or more compounds according to the invention, the liquid-crystalline media according to the invention preferably contain, as further components, 2 to 40, in particular 4 to 30, components. Besides one or more compounds according to the invention, these media very particularly preferably contain 7 to 25 components. These further components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoate, cyclohexanecarboxylate and cyclohexylcyclohexanecarboxylate, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds which are suitable as further components of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In formulae 1, 2, 3, 4 and 5, L and E, which may be identical or different and are in each case independent of one another, are a bivalent radical from the group formed from —Phe—, —Cyc—, —Phe—Phe—, —Phe—Cyc—, —Cyc—Cyc—, —Pyr—, —Dio—, —G—Phe— and —G—Cyc— and the mirror images thereof, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5, in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and, if appropriate, one or more components selected from the compounds of the formulae 1, 2, 3, 4 and 5 in which the radicals L and E are selected from the group comprising —Phe—Cyc—, —Cyc—Cyc—, —G—Phe— and —G—Cyc—. In the compounds of the sub-formulae 1a, 2a, 3a, 4a and 5a, R' and R'', in each case independently of one another, are alkyl, alkenyl, alkoxy, alkenyloxy or alkanoyloxy having up to 8 carbon atoms. In most of these compounds, R' and R'' are different from one another, one of these radicals usually being alkyl or alkenyl. In the compounds of the sub-formulae 1b, 2b, 3b, 4b and 5b, R'' is —CN, —CF$_3$, F, Cl or —NCS; in these formulae, R has the meaning indicated in the case of the compounds of the sub-formulae 1a to 5a and is preferably alkyl or alkenyl. However, other variants of the proposed substituents in the compounds of the formulae 1, 2, 3, 4 and 5 are common. Many such substances and also mixtures thereof are commercially available. All these substances can be obtained by methods known from the literature or analogously thereto.

Besides components from the group comprising the compounds 1a, 2a, 3a, 4a and 5a (group 1), the media according to the invention preferably also contain components from the group comprising the compounds 1b, 2b, 3b, 4b and 5b (group 2), whose proportions are preferably as follows:
Group 1: 20 to 90%, in particular 30 to 90%,
Group 2: 10 to 80%, in particular 10 to 50%,
the sum of the proportions of the compounds according to the invention and of the compounds from groups 1 and 2 adding up to 100%.

The media according to the invention preferably contain 1 to 40%, in particular preferably 5 to 30%, of compounds according to the invention. Additionally preferred media are those which contain more than 40%, in particular 45 to 90%, of compounds according to the invention. The media preferably contain three, four or five compounds according to the invention.

The media according to the invention are prepared in a manner customary per se. In general, the components are dissolved in one another, expediently at elevated temperature. By means of suitable additives, the liquid-crystalline phases according to the invention can be modified in a manner such that they can be used in all types of liquid-crystal display elements disclosed hitherto. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the preparation of coloured guest/host systems, or substances can be added to modify the dielectric anisotropy, the viscosity and/or the orientation of the nematic phases.

The examples below are intended to illustrate the invention without representing a limitation. mp.=melting point, cp. clear point. Above and below, percentages are percent by weight; all temperatures are given in degrees Celsius. "Customary work-up" means that water is added, the mixture is extracted with methylene chloride, the organic phase is separated off, dried and evaporated, and the product is purified by crystallization and/or chromatography.

In addition, the abbreviations have the following meanings:
C: crystalline-solid state, S: smectic phase (the index characterizes the phase type), N: nematic state, Ch: cholesteric phase, I: isotropic phase. The number between two symbols indicates the conversion temperature in degrees Celsius.

EXAMPLE 1

0.1 mol of 2,3-difluoro-4-ethoxyphenol (preparable from 2,3-difluorophenol by alkylation using diethyl sulphate/potassium carbonate in dimethylformamide, lithiation at −70° to −80°, reaction with N-methylpiperidine and oxidation of the aldehyde by the Baeyer-Villiger method using performic acid) and 0.1 mol of pyridine were dissolved in 100 ml of toluene. 0.1 mol of trans-4-pentylcyclohexanecarbonyl chloride is added dropwise at 80°, and the mixture is stirred for a further 3 hours. The pyridine hydrochloride precipitated is filtered off with suction, the toluene is removed by distillation, and the 2,3-difluoro-4-ethoxyphenyl trans-4-pentylcyclohexanoate remaining is purified by crystallization from ethanol, mp. 48°, cp. 62.5°.

The following are prepared analogously:
2,3-difluoro-4-ethoxyphenyl trans-4-propylcyclohexanoate, mp. 50°, cp. 52°
2,3-difluoro-4-ethoxyphenyl trans-4-ethylcyclohexanoate
2,3-difluoro-4-ethoxyphenyl trans-4-butylcyclohexanoate, C 59° N (48°) I
2,3-difluoro-4-ethoxyphenyl trans-4-heptylcyclohexanoate, C 53° N 66° I
2,3-difluoro-4-methoxyphenyl trans-4-ethylcyclohexanoate
2,3-difluoro-4-methoxyphenyl trans-4-propylcyclohexanoate
2,3-difluoro-4-methoxyphenyl trans-4-butylcyclohexanoate
2,3-difluoro-4-methoxyphenyl trans-4-pentylcyclohexanoate
2,3-difluoro-4-methoxyphenyl trans-4-heptylcyclohexanoate
2,3-difluoro-4-propoxyphenyl trans-4-ethylcyclohexanoate
2,3-difluoro-4-propoxyphenyl trans-4-propylcyclohexanoate
2,3-difluoro-4-propoxyphenyl trans-4-butylcyclohexanoate 2,3-difluoro-4-propoxyphenyl trans-4-pentylcyclohexanoate
2,3-difluoro-4-propoxyphenyl trans-4-heptylcyclohexanoate
2,3-difluoro-4-butoxyphenyl trans-4-ethylcyclohexanoate
2,3-difluoro-4-butoxyphenyl trans-4-propylcyclohexanoate
2,3-difluoro-4-butoxyphenyl trans-4-butylcyclohexanoate
2,3-difluoro-4-butoxyphenyl trans-4-pentylcyclohexanoate
2,3-difluoro-4-butoxyphenyl trans-4-heptylcyclohexanoate
2,3-difluoro-4-hexoxyphenyl trans-4-ethylcyclohexanoate
2,3-difluoro-4-hexoxyphenyl trans-4-propylcyclohexanoate
2,3-difluoro-4-hexoxyphenyl trans-4-butylcyclohexanoate
2,3-difluoro-4-hexoxyphenyl trans-4-pentylcyclohexanoate
2,3-difluoro-4-hexoxyphenyl trans-4-heptylcyclohexanoate
2,3-difluoro-4-octoxyphenyl trans-4-ethylcyclohexanoate
2,3-difluoro-4-octoxyphenyl trans-4-propylcyclohexanoate
2,3-difluoro-4-octoxyphenyl trans-4-pentylcyclohexanoate
2,3-difluoro-4-octoxyphenyl trans-4-heptylcyclohexanoate, C 43° N 64° I.

EXAMPLE 2

2,3-difluoro-4-ethoxyphenyl trans-4-(trans-4propylcyclohexyl)cyclohexanoate, C 88° $S_A$ 100° N 223° I, is obtained analogously to Example 1 from the same phenol by reaction with 4-(trans-4-propylcyclohexyl)cyclohexanecarbonyl chloride.

The following are prepared analogously:
2,3-difluoro-4-ethoxyphenyl trans-4-(trans-4-ethylcyclohexyl)-cyclohexanoate
2,3-difluoro-4-ethoxyphenyl trans-4-(trans-4-butylcyclohexyl)-cyclohexanoate, C 91° $S_B$ 109° $S_A$ 128° N 217° I
2,3-difluoro-4-ethoxyphenyl trans-4-(trans-4-pentylcyclohexyl)-cyclohexanoate, C 95° $S_B$ 119° $S_A$ 143° N 220° I
2,3-difluoro-4-ethoxyphenyl trans-4-(trans-4-heptylcyclohexyl)-cyclohexanoate
2,3-difluoro-4-methoxyphenyl trans-4-(trans-4-ethylcyclohexyl)-cyclohexanoate
2,3-difluoro-4-methoxyphenyl trans-4-(trans-4-propylcyclohexyl)-cyclohexanoate
2,3-difluoro-4-methoxyphenyl trans-4-(trans-4-butylcyclohexyl)-cyclohexanoate
2,3-difluoro-4-methoxyphenyl trans-4-(trans-4-pentylcyclohexyl)-cyclohexanoate
2,3-difluoro-4-methoxyphenyl trans-4-(trans-4-heptylcyclohexyl)-cyclohexanoate
2,3-difluoro-4-propoxyphenyl trans-4-(trans-4-ethylcyclohexyl)-cyclohexanoate
2,3-difluoro-4-propoxyphenyl trans-4-(trans-4-propylcyclohexyl)-cyclohexanoate
2,3-difluoro-4-propoxyphenyl trans-4-(trans-4-butylcyclohexyl)-cyclohexanoate
2,3-difluoro-4-propoxyphenyl trans-4-(trans-4-pentylcyclohexyl)-cyclohexanoate
2,3-difluoro-4-propoxyphenyl trans-4-(trans-4-heptylcyclohexyl)-cyclohexanoate
2,3-difluoro-4-butoxyphenyl trans-4-(trans-4-ethylcyclohexyl)-cyclohexanoate
2,3-difluoro-4-butoxyphenyl trans-4-(trans-4-propylcyclohexyl)-cyclohexanoate
2,3-difluoro-4-butoxyphenyl trans-4-(trans-4-butylcyclohexyl)-cyclohexanoate
2,3-difluoro-4-butoxyphenyl trans-4-(trans-4-pentylcyclohexyl)-cyclohexanoate
2,3-difluoro-4-butoxyphenyl trans-4-(trans-4-heptylcyclohexyl)-cyclohexanoate

EXAMPLE 3

0.1 mol of 4-hexyloxybenzoic acid, 0.01 mol of dimethylaminopyridine and 0.1 mol of 2,3-difluoro-4octyloxyphenol (preparable from 2,3-difluorooctyloxybenzene by lithiation at −70° to −80° and dropwise addition of a solution of lithium t-butylperoxide in ether prepared from 0.12 mol of t-butyl hydroperoxide and 0.12 mol of butyllithium) are introduced into 150 ml of dichloromethane, a solution of 0.1 mol of dicyclohexylcarbodiimide in 30 ml of dichloromethane is added dropwise with stirring at 10o, and the mixture is subsequently stirred at room temperature for 15 hours. The mixture is filtered through silica gel, the solvent is evaporated, and 2,3-difluoro-4-octyloxyphenyl 4-hexyloxybenzoate is obtained as the residue.

The following are prepared analogously:
2,3-difluoro-4-octyloxyphenyl p-(4-heptyloxy-3-fluorophenyl)benzoate, C 69.3°, $S_C$ 146 $S_A$ 152.7° N 156° I
2,3-difluoro-4-octyloxyphenyl p-(4-octyloxy-3-fluorophenyl)benzoate
2,3-difluoro-4-octyloxyphenyl p-(4-nonyloxy-3-fluorophenyl)benzoate, C 71.7° $S_C$ 14 $S_A$ 149.8° N 150.2 I
2,3-difluoro-4-octyloxyphenyl p-(4-decyloxy-3-fluorophenyl)benzoate
2,3-difluoro-4-octyloxyphenyl p-(4-heptyl-3-fluorophenyl)benzoate, C 81° $S_C$ 121° $S_A$ 128.5N 148° I
4-heptyloxy-2,3-difluorophenyl p-hexylbenzoate
4-heptyloxy-2,3-difluorophenyl p-heptylbenzoate
4-heptyloxy-2,3-difluorophenyl p-octylbenzoate, mp 43.5°
4-heptyloxy 2,3-difluorophenyl p-decylbenzoate
4-heptyloxy-2,3-difluorophenyl p-hexyloxybenzoate
4-heptyloxy-2,3-difluorophenyl p-heptyloxybenzoate
4-heptyloxy 2,3-difluorophenyl p-octyloxybenzoate, C 53° ($S_C$ 39°) N 57° I
2,3-difluoro-4-heptyloxyphenyl p-(4-hexyl-3-fluorophenyl)benzoate
2,3-difluoro-4-heptyloxyphenyl p-(4-heptyl-3-fluorophenyl)benzoate
2,3-difluoro-4-heptyloxyphenyl p-(4-octyl-3-fluorophenyl)benzoate, C 60° $S_C$ 15 $S_A$ 155° N 157° I
2,3-difluoro-4-heptyloxyphenyl p-(4-hexylphenyl)benzoate,
2,3-difluoro-4-heptyloxyphenyl p-(4-heptylphenyl)benzoate
2,3-difluoro-4-heptyloxyphenyl p-(4-octylphenyl)benzoate, C 86° $S_C$ 12 $S_A$ 131° N 145° I
2,3-difluoro-4-heptyloxyphenyl p-(4-hexyloxyphenyl)benzoate
2,3-difluoro-4-heptyloxyphenyl p-(4-heptyloxyphenyl)benzoate
2,3-difluoro-4-heptyloxyphenyl p-(4-octyloxyphenyl)benzoate, C 94° $S_C$ 157° $S_A$ 166° N 174° I
4-octyloxy-2,3-difluorophenyl p-hexylbenzoate
4-octyloxy-2,3-difluorophenyl p-heptylbenzoate 4-octyloxy-2,3-difluorophenyl p-octylbenzoate
4-octyloxy-2,3-difluorophenyl p-nonylbenzoate
4-octyloxy-2,3-difluorophenyl p-hexyloxybenzoate
4-octyloxy-2,3-difluorophenyl p-heptyloxybenzoate, C 45° N 53° I
4-octyloxy-2,3-difluorophenyl p-octyloxybenzoate, C 53° S$_C$ (39°) N 59.8° I
4-octyloxy-2,3-difluorophenyl p-nonyloxybenzoate, C 53.6° S$_C$ (49°) N 59.3° I
4-octyloxy-2,3-difluorophenyl trans-4-pentylcyclohexylcarboxylate, C 30° N 60° I
4-octyloxy-2,3-difluorophenyl trans,trans-4'-pentylbicyclohexyl-4-ylcarboxylate, C 58° S$_C$ (38°) S$_A$ 167° N 182.5° I
4-octyloxy-2,3-difluorophenyl 4-(trans-4-pentylcyclohexyl)benzoate, C 62° S$_C$ 63° S$_A$ 100° N 152.2° I
2,3-difluoro-4-nonyloxyphenyl p-(4-heptyloxy-3-fluorophenyl)benzoate
2,3-difluoro-4-nonyloxyphenyl p-(4-octyloxy-3-fluorophenyl)benzoate
2,3-difluoro-4-nonyloxyphenyl p-(4-nonyloxy-3-fluorophenyl)benzoate
2,3-difluoro-4-nonyloxyphenyl p-(4-decyloxy-3-fluorophenyl)benzoate
2,3-difluoro-4-decyloxyphenyl p-(4-heptyloxy-3-fluorophenyl)benzoate
2,3-difluoro-4-decyloxyphenyl p-(4-octyloxy-3-fluorophenyl)benzoate
2,3-difluoro-4-decyloxyphenyl p-(4-nonyloxy-3-fluorophenyl)benzoate
2,3-difluoro-4-decyloxyphenyl p-(4-decyloxy-3-fluorophenyl)benzoate

EXAMPLE 4

1 mol of 2,3-difluorophenol is dissolved in 2 l of 10% sodium hydroxide solution, and a saturated aqueous solution of potassium peroxodisulphate is added dropwise at 20° over the course of 3-4 hours. After the solution has been left to stand overnight, it is slightly acidified (pH 3-4), and unreacted starting material is extracted with ether. The aqueous phase is neutralized using sodium hydrogen carbonate and evaporated to dryness in vacuo. 2,3-difluoro-4-hydroxyphenylpotassium sulphate is dissolved out of the residue using 90% ethanol, and the alcohol is evaporated.

14 g of benzyl chloride are added dropwise with stirring and refluxing to 25 g of the crude product (~0.1 mol) in aqueous-alcoholic sodium hydroxide solution (7 g of NaOH in 100 ml of 50% alcohol). The reaction is left to continue for 2 hours, and the mixture is slightly acidified using hydrochloric acid and heated for a further 2 hours. After cooling, 4-benzyloxy-2,3-difluorophenol is extracted and distilled after the solvent has been stripped off.

Monoalkyl ethers of 2,3-difluorohydroquinone are obtained analogously by reacting 2,3-difluoro-4-hydroxyphenylpotassium sulphate with alkyl bromides and sulphates.

0.1 mol of 2,3-difluoro-4-benzyloxyphenol are esterified using 0.1 mol of pyridine and 0.1 mol of 4-ethoxybenzoyl chloride in toluene, the resultant ester is isolated, the benzyl ether is subsequently cleaved hydrogenolytically using palladium/charcoal as catalyst.

2,3-Difluoro-4-butyryloxyphenyl 4-ethoxybenzoate is obtained by esterification of the free hydroxyl group using butyric acid/dicyclohexylcarbodiimide.

EXAMPLE 5

2,3-Difluoro-4-octanoyloxyphenyl 2-fluoro-4-(5-hexylpyrimidin-2-yl)benzoate is obtained analogously to Example 4 by esterification of 2,3-difluoro-4-benzyloxyphenol using 2-fluoro-4-(5-hexylpyrimidin-2-yl)benzoic acid (prepared by hydrolysis of the nitrile via the imidoester) and dicyclohexylcarbodiimide, hydrogenolytic cleavage of the benzyl ether and reesterification using octanoic acid.

EXAMPLE 6

0.1 mol of 2,3-difluoro-4-(trans-4-pentylcyclohexyl)-methoxyphenol, 0.11 mol of butyl bromide and 0.11 mol of potassium carbonate are heated for 16 hours at 100° in 100 ml of dimethylformamide (DMF). After cooling, the inorganic salts are filtered off with suction, the filtrate is concentrated, and water is added. 1-butyloxy-2,3-difluoro-4-(trans-4-pentylcyclohexyl)methoxybenzene is obtained by extraction with dichloromethane.

The following are prepared analogously:
1-ethoxy-2,3-difluoro-4-(trans-4-pentylcyclohexyl)methoxybenzene, C 38° N (0°) I
1-ethoxy-2,3-difluoro-4-[trans-4-(trans-4-propylcyclohexyl)-cyclohexyl]methoxybenzene, C 63° N 153° I.
1-ethoxy-2,3-difluoro-4-[trans-4-(trans-4-butylcyclohexyl)-cyclohexyl]methoxybenzene
1-ethoxy-2,3-difluoro-4-[trans-4-(trans-4-pentylcyclohexyl)-cyclohexyl]methoxybenzene
1-methoxy-2,3-difluoro-4-[trans-4-(trans-4-ethylcyclohexyl)-cyclohexyl]methoxybenzene
1-methoxy-2,3-difluoro-4-[trans-4-(trans-4-propylcyclohexyl)-cyclohexyl]methoxybenzene
1-methoxy-2,3-difluoro-4-[trans-4-(trans-4-butylcyclohexyl)-cyclohexyl]methoxybenzene
1-methoxy-2,3-difluoro-4-[trans-4-(trans-4-pentylcyclohexyl)-cyclohexyl]methoxybenzene
1-methoxy-2,3-difluoro-4-[trans-4-(trans-4-heptylcyclohexyl)-cyclohexyl]methoxybenzene
1-propoxy-2,3-difluoro-4-[trans-4-(trans-4-ethylcyclohexyl)-cyclohexyl]methoxybenzene
1-propoxy-2,3-difluoro-4-[trans-4-(trans-4-propylcyclohexyl)-cyclohexyl]methoxybenzene
1-propoxy-2,3-difluoro-4-[trans-4-(trans-4-butylcyclohexyl)-cyclohexyl]methoxybenzene
1-propoxy-2,3-difluoro-4-[trans-4-(trans-4-pentylcyclohexyl)-cyclohexyl]methoxybenzene
1-propoxy-2,3-difluoro-4-[trans-4-(trans-4-heptylcyclohexyl)-cyclohexyl]methoxybenzene
1-butoxy-2,3-difluoro-4-[trans-4-(trans-4-ethylcyclohexyl)-cyclohexyl]methoxybenzene
1-butoxy-2,3-difluoro-4-[trans-4-(trans-4-propylcyclohexyl)-cyclohexyl]methoxybenzene
1-butoxy-2,3-difluoro-4-[trans-4-(trans-4-butylcyclohexyl)-cyclohexyl]methoxybenzene
1-butoxy-2,3-difluoro-4-[trans-4-(trans-4-pentylcyclohexyl)-cyclohexyl]methoxybenzene
1-butoxy-2,3-difluoro-4-[trans-4-(trans-4-heptylcyclohexyl)-cyclohexyl]methoxybenzene

EXAMPLE 7

1-[trans-4-(trans-4-propylcyclohexyl)cyclohexylmethoxy]-2,3-difluoro-4-(trans-4-pentylcyclohexylmethoxy)benzene is obtained by the procedure of Example 6 from 0.1 mol of 2,3-difluoro-4-(trans-4-pentylcyclohexyl)methoxyphenol, 0.1 mol of trans-4-(trans-4-propylcyclohexyl)cyclohexylmethyl iodide and 0.1 mol of potassium carbonate.

EXAMPLE 8

1 mol of 2,3-difluorophenol is dissolved in 1 l of 10% sodium hydroxide solution, and a saturated aqueous solution of 1.1 mol of potassium peroxodisulphate is added dropwise over the course of 4 hours with ice cooling. During this addition, the temperature must not exceed 20o The mixture is stirred overnight at room temperature and neutralized using hydrochloric acid, and unreacted starting material is extracted with ether. 3 l of toluene and 2 mol of sodium sulphite are added to the aqueous phase, and the mixture is strongly acidified using 1 l of concentrated hydrochloric acid and refluxed for 20 minutes. After cooling, the toluene layer is separated off, the aqueous phase is extracted with ether in a perforator, and 2,3-difluorohydroquinone is obtained by evaporating the combined toluene and ether extracts.

EXAMPLE 9

0.05 mol of 2,3-difluorohydroquinone and 0.1 mol of pyridine are dissolved in 100 ml of toluene. 0.1 mol of trans-4-butylcyclohexanecarbonyl chloride is added dropwise at 80°, and the mixture is stirred for a further 3 hours. Customary work-up gives 2,3-difluoro-1,4-bis(-trans-4-butylcyclohexylcarbonyloxy)benzene.

The following are prepared analogously:
2,3-difluoro-1,4-bis-(trans-4-propylcyclohexylcarbonyloxy)benzene
2,3-difluoro-1,4-bis-(trans-4-pentylcyclohexylcarbonyloxy)benzene, C 87° N 208° I
2,3-difluoro-1,4-bis-(trans-4-hexylcyclohexylcarbonyloxy)benzene
2,3-difluoro-1,4-bis-(trans-4-heptylcyclohexylcarbonyloxy)benzene
2,3-difluoro-1,4-bis-(trans-4-octylcyclohexylcarbonyloxy)benzene, C 80° $S_F$ 94° $S_I$ 105° $S_C$ 124° N 176° I
2,3-difluoro-1,4-bis-(trans-4-nonylcyclohexylcarbonyloxy)benzene
2,3-difluoro-1,4-bis-(trans-4-decylcyclohexylcarbonyloxy)benzene

EXAMPLE 10

Analogously to Example 4, 2,3-difluoro-1-(trans-4-propylcyclohexanoyloxy)-4-(trans-4-pentylcyclohexanoyloxy)benzene is obtained by reaction of 2,3-difluoro-4-benzyloxyphenol with trans-4-propylcyclohexanecarbonyl chloride/pyridine, hydrogenolytic cleavage of the benzyl ether and re-esterification using trans-4-pentylcyclohexanecarboxylic acid/dicyclohexylcarbodiimide in the presence of 4-dimethylaminopyridine.

The following examples relate to liquid-crystalline phases containing at least one compound according to the invention:

EXAMPLE A

A liquid-crystalline phase comprising
6% of 4-octyloxyphenyl 4-decyloxybenzoate,
9% of 4-nonyloxyphenyl 4-decyloxybenzoate,
14% of 4-decyloxyphenyl 4-decyloxybenzoate,
5% of 2,3-difluoro-4-octyloxyphenyl 4-octyloxybenzoate
7% of 2,3-difluoro-4-octyloxyphenyl 4-decyloxybenzoate
9% of 2,3-difluoro-4-decyloxyphenyl 4-decyloxybenzoate
4% of 2,3-difluoro-4-nonanoyloxyphenyl 4-octyloxybenzoate
10% of 4'-pentyloxybiphenyl-4-yl 4-octyloxybenzoate
8% of 4'-heptyloxybiphenyl-4-yl 4-octyloxybenzoate
17% of r-1-cyano-cis-4-(4'-octyloxybiphenyl-4-yl)-1-octylcyclohexane and
11% of chiral p-(5-heptylpyrimidin-2-yl)phenyl 2-chloro-3-methylbutyrate
exhibits $S_C^*$ 62 $S_A$ 68 Ch 81 I and a spontaneous polarization of 13 nC/cm$^2$ at room temperature.

EXAMPLE B

A liquid-crystalline phase comprising
8% of 2-p-octyloxyphenyl-5-octylpyrimidine
10% of 2-p-nonyloxyphenyl-5-octylpyrimidine
12% of 2-p-octyloxyphhase comprising imidine
20% of 2-p-nonyloxyphenyl-5-nonylpyrimidine
7% of 2,3-difluoro-4-decyloxyphenyl 4-decyloxybenzoate
7% of 2,3-difluoro-4-octyloxyphenyl 4-decyloxybenzoate
9% of 2-(p-heptylphenyl)-5-(p-hexyloxyphenyl)-1,3,4-thiadiazole
9% of 2-(p-heptylphenyl)-5-(p-octyloxyphenyl)-1,3,4-thiadiazole
8% of 2,3-difluoro-4-octanoyloxyphenyl 4-(5-hexylpyrimidin-2-yl)-2-fluorobenzoate and
10% of chiral isopropyl 2-[p-(p-decyloxyphenyl)-phenoxy]propionate
exhibits $S_C^*$ 58 $S_A$ and a spontaneous polarization of 11 nC/cm$^2$ at room temperature.

EXAMPLE C

A nematic liquid-crystalline phase comprising
7% of 2-p-cyanophenyl-5-propyl-13-dioxane,
7% of 2-p-cyanophenyl-5-butyl-1,3-dioxane,
6% of 2-p-cyanophenyl-5-pentyl-1,3-dioxane,
10% of trans-1-p-propylphenyl-4-pentylcyclohexane
8% of 4-cyano-4'-(trans-4-pentylcyclohexyl)biphenyl,
6% of 4-ethyl-4'-(trans-4-pentylcyclohexyl)biphenyl,
4% of 4-ethyl-4'-(trans-4-propylcyclohexyl)biphenyl,
5% of 2-p-pentyloxyphenyl-5-hexylpyrimidine,
6% of 2-p-heptyloxyphenyl-5-hexylpyrimidine,
5% of 2-p-methoxyphenyl-5-hexylpyrimidine,
8% of 2-p-heptyloxyphenyl-5-heptylpyrimidine,
8% of 2-p-nonyloxyphenyl-5-heptylpyrimidine,
4% of p-methoxyphenyl trans-4-propylcyclohexanecarboxylate
7% of 2,3-difluoro-4-ethoxyphenyl trans-4-pentylcyclohexanoate,
5% of 2,3-difluoro-4-ethoxyphenyl trans-4-(trans-4-propylcyclohexyl)cyclohexanoate and
4% of p-trans-4-propylcyclohexyphenyl butyrate is distinguished by good multiplex properties.

EXAMPLE D

A liquid-crystalline phase comprising 12.5% of 4-heptyloxy-2,3-difluorophenyl 4'-octyloxybiphenyl-4-ylcarboxylate
14.2% of 4-heptyloxy-2,3-difluorophenyl 4-octyloxybenzoate
12.5% of 4-heptyl-2-fluorophenyl 4'-heptyloxybiphenyl-4-ylcarboxylate
12.5% of 4-heptyl-2-fluorophenyl 4'-heptyloxy-2'-fluorobiphenyl-4-ylcarboxylate 14.2% of 4-octyloxy-3-fluorophenyl 4-octyloxybenzoate 12.34% of 4-pentyl-2-fluorophenyl 4-octyloxybenzoate 14.24% of 4-octyloxy-3-fluorophenyl 4-heptyloxybenzoate 5.04% of chiral 4-(2-methylbutyl)-phenyl 4'-octylbiphenyl-4-ylcarboxylate and 2.48% of chiral 1-cyano-2-methylpropyl 4'-octyloxybiphenyl-4-ylcarboxylate exhibits $S_C^*$ 66.4° $S_A$ 73° Ch 97.2° I and a spontaneous polarization of 9 nC/cm² at 30° C.

EXAMPLE E

A liquid-crystalline phase comprising 16.87% of 4-heptyl-2-fluorophenyl 4'-heptyloxybiphenyl-4-ylcarboxylate 16.87% of 4-heptyl-2-fluorophenyl 4,-heptyloxy-2'-fluorobiphenyl-4-ylcarboxylate 16.87% of 4-octyl-2-fluorophenyl 4,-octyloxy-2',3'-difluorobiphenyl-4-ylcarboxylate 14% of 4-octyloxy-3-fluorophenyl 4-octyloxybenzoate 14% of 4-hexyloxy-3-fluorophenyl 4-octyloxybenzoate 10% of 4-octyloxy-2-fluorophenyl 4-pentylbenzoate 9% of 4-heptyl-3-fluorophenyl 4'-octyloxy-2',3'-difluorobiphenyl-4-ylcarboxylate and 2.4% of chiral 1-cyano-2-methylpropyl 4'-octyloxybiphenyl-4-ylcarboxylate exhibits $S_C^*$ 71.8° $S_A$ 81° Ch 103.8° I and a high spontaneous polarization.

We claim:

1. A 2,3-difluorohydroquinone compound of the formula I,

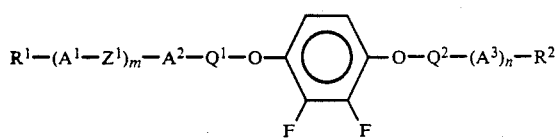

wherein

R¹ and R², in each case independently of one another, are alkyl having 1 to 15 C atoms or a alkenyl having 3 to 15 C atoms which are unsubstituted, monosubstituted by cyano or at least monosubstituted by fluorine or chlorine, it also being possible for one CH₂ group in these radicals to be replaced by —O—, —CO—, —CO—O—, —O—CO— or —O—CO—O—;

A¹, A² and A³ in each case are independently trans-1,4-cyclohexylene;

Z¹ is —CO—O—, —O—CO—, —CH₂—CH₂13 , —OCH₂—, —CH₂O—, —C≡C— or a single bond;

Q¹ and Q², in each case independently of one another, are —CO— or —CH₂—;

m and n are each 0, 1 or 2; and (m+n) is 0, 1 or 2.

2. A 2,3-difluorohydroquinone compound of claim 1, wherein m is 0 or 1 and Z¹ is —CH₂CH₂— or a single bond.

3. A 2,3-difluorohydroquinone compound of claim 1, wherein R¹ and R² in each case are, independently of one another, straight-chain alkyl of 2 to 7 C atoms.

4. A 2,3-difluorohydroquinone compound of claim 1, wherein n is 0.

5. A 2,3-difluorohydroquinone compound of claim 4, wherein m is 1 or 2.

6. A 2,3-difluorohydroquinone compound, wherein said compound is:

2,3-difluoro-4-ethoxyphenyl trans-4-pentylcyclohexanoate, 2,3-difluoro-4-ethoxyphenyl trans-4-propylcyclohexanoate, 2,3-difluoro-4-ethoxyphenyl trans-4-ethylcyclohexanoate,, 2,3-difluoro-4-ethoxyphenyl trans-4-butylcyclohexanoate, 2,3-difluoro-4-ethoxyphenyl trans-4-heptylcyclohexanoate, 2,3-difluoro-4-methoxyphenyl trans-4-ethylcyclohexanoate, 2,3-difluoro-4-methoxyphenyl trans-4-propylcyclohexanoate, 2,3-difluoro-4-methoxyphenyl trans-4-butylcyclohexanoate, 2,3-difluoro-4-methoxyphenyl trans-4-pentylcyclohexanoate, 2,3-difluoro-4-methoxyphenyl trans-4-heptylcyclohexanoate, 2,3-difluoro-4-propoxyphenyl trans-4-ethylcyclohexanoate, 2,3-difluoro-4-propoxyphenyl trans-4-propylcyclohexanoate, 2,3-difluoro-4-propoxyphenyl trans-4-butylcyclohexanoate, 2,3-difluoro-4-propoxyphenyl trans-4-pentylcyclohexanoate, 2,3-difluoro-4-propoxyphenyl trans-4-heptylcyclohexanoate, 2,3-difluoro-4-butoxyphenyl trans-4-ethylcyclohexanoate, 2,3-difluoro-4-butoxyphenyl trans-4-propylcyclohexanoate, 2,3-difluoro-4-butoxyphenyl trans-4-butylcyclohexanoate, 2,3-difluoro-4-butoxyphenyl trans-4-pentylcyclohexanoate, 2,3-difluoro-4-butoxyphenyl trans-4-heptylcyclohexanoate, 2,3-difluoro-4-hexoxyphenyl trans-4-ethylcyclohexanoate, 2,3-difluoro-4-hexoxyphenyl trans-4-propylcyclohexanoate, 2,3-difluoro-4-hexoxyphenyl trans-4-butylcyclohexanoate, 2,3-difluoro-4-hexoxyphenyl trans-4-pentylcyclohexanoate, 2,3-difluoro-4-hexoxyphenyl trans-4-heptylcyclohexanoate, 2,3-difluoro-4-octoxyphenyl trans-4-ethylcyclohexanoate, 2,3-difluoro-4-octoxyphenyl trans-4-propylcyclohexanoate, 2,3-difluoro-4-octoxyphenyl trans-4-butylcyclohexanoate, 2,3-difluoro-4-octoxyphenyl trans-4-heptylcyclohexanoate, 2,3-difluoro-4-ethoxyphenyl trans-4-(trans-4-propylcyclohexyl)-cyclohexanoate, 2,3-difluoro-4-ethoxyphenyl trans-4-(trans-4-ethylcyclohexyl)-cyclohexanoate, 2,3-difluoro-4-ethoxyphenyl trans-4-(trans-4-butylcyclohexyl)-cyclohexanoate, 2,3-difluoro-4-ethoxyphenyl trans-4-(trans-4-pentylcyclohexyl)-cyclohexanoate, 2,3-difluoro-4-ethoxyphenyl trans-4-(trans-4-heptylcyclohexyl)-cyclohexanoate,
2,3-difluoro-4-methoxyphenyl trans-4-(trans-4-ethylcyclohexyl)-cyclohexanoate,
2,3-difluoro-4-methoxyphenyl trans-4-(trans-4-propylcyclohexyl)-cyclohexanoate,
2,3-difluoro-4-methoxyphenyl trans-4-(trans-4-butylcyclohexyl)-cyclohexanoate,
2,3-difluoro-4-methoxyphenyl trans-4-(trans-4-pentylcyclohexyl)-cyclohexanoate,
2,3-difluoro-4-methoxyphenyl trans-4-(trans-4-heptylcyclohexyl)-cyclohexanoate,
2,3-difluoro-4-propoxyphenyl trans-4-(trans-4-ethylcyclohexyl)-cyclohexanoate,
2,3-difluoro-4-propoxyphenyl trans-4-(trans-4-propylcyclohexyl)-cyclohexanoate,
2,3-difluoro-4-propoxyphenyl trans-4-(trans-4-butylcyclohexyl)-cyclohexanoate,
2,3-difluoro-4-propoxyphenyl trans-4-(trans-4-pentylcyclohexyl)-cyclohexanoate,
2,3-difluoro-4-propoxyphenyl trans-4-(trans-4-heptylcyclohexyl)-cyclohexanoate,
2,3-difluoro-4-butoxyphenyl trans-4-(trans-4-ethylcyclohexyl)-cyclohexanoate,
2,3-difluoro-4-butoxyphenyl trans-4-(trans-4-propylcyclohexyl)-cyclohexanoate,
2,3-difluoro-4-butoxyphenyl trans-4-(trans-4-butylcyclohexyl)-cyclohexanoate,
2,3-difluoro-4-butoxyphenyl trans-4-(trans-4-pentylcyclohexyl)-cyclohexanoate, or
2,3-difluoro-4-butoxyphenyl trans-4-(trans-4-heptylcyclohexyl)-cyclohexanoate.

7. A 2,3-difluorohydroquinone compound of claim 1, wherein at least one of $Q^1$ and $Q^2$ is —$CH_2$—.

8. A 2,3-difluorohydroquinone compound of claim 1, wherein $Q^1$ is —$CH_2$—.

9. A 2,3-difluorohydroquinone compound of claim 1, wherein at least one of $R^1$ and $R^2$ is alkenyl or oxaalkyl.

10. In a liquid-crystalline medium comprising at least two liquid-crystalline components, the improvement wherein at least one component is a compound according to claim 6.

11. In an electrooptical display element, comprising a dielectric, the improvement wherein said dielectric is a medium according to claim 10.

12. In a liquid-crystalline medium comprising at least two liquid-crystalline components, the improvement wherein at least one component is a compound according to claim 1.

13. In an electrooptical display element, comprising a dielectric, the improvement wherein said dielectric is a medium according to claim 12.

* * * * *